(12) United States Patent
Butzbacker et al.

(10) Patent No.: US 10,682,172 B2
(45) Date of Patent: Jun. 16, 2020

(54) ELECTROCHEMICAL PROTECTION OF CONDUCTING CIRCUIT IN THE BODY OF A PATIENT

(71) Applicant: COOK MEDICAL TECHNOLOGIES LLC, Bloomington, IN (US)

(72) Inventors: Raimo Urban Butzbacker, Haslev (DK); Rune T. Paamand, Vanloese (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 158 days.

(21) Appl. No.: 15/379,683

(22) Filed: Dec. 15, 2016

(65) Prior Publication Data

US 2017/0172644 A1   Jun. 22, 2017

(30) Foreign Application Priority Data

Dec. 18, 2015   (GB) .................................. 1522353.0

(51) Int. Cl.
*A61B 18/04* (2006.01)
*A61B 18/10* (2006.01)
(Continued)

(52) U.S. Cl.
CPC ........ *A61B 18/10* (2013.01); *A61B 17/12022* (2013.01); *A61B 18/08* (2013.01);
(Continued)

(58) Field of Classification Search
CPC . A61B 17/12022; A61B 18/08; A61B 18/082; A61B 18/10; A61B 2017/00132;
(Continued)

(56) References Cited

U.S. PATENT DOCUMENTS

| 4,181,131 A | * | 1/1980 | Ogiu | A61B 18/14 606/47 |
| 5,103,804 A | * | 4/1992 | Abele | A61B 18/08 600/104 |

(Continued)

FOREIGN PATENT DOCUMENTS

| EP | 0707830 A1 | 4/1996 |
| EP | 0 750 886 A1 | 1/1997 |

OTHER PUBLICATIONS

European Extended Examination Report for EP16275172.1, dated May 18, 2017.
(Continued)

*Primary Examiner* — Daniel W Fowler
(74) *Attorney, Agent, or Firm* — Brinks Gilson & Lione

(57) ABSTRACT

The preferred embodiment provides apparatus for ablating a vessel by generating heat within a vessel to cause blood clotting to occlude the vessel. The apparatus includes an electrically resistive element at the distal end of the apparatus, the resistive element being uncoated and therefore in bare form. An alternating current supply feeds electrical current through the resistive element to cause heating of the element and surrounding blood or tissue. The alternating current power supply preferably is balanced about a centre point so as to create a net sum of alternating pulses of zero. It has been found that the supply of alternating current to the resistive element reduces or eliminates corrosion of the resistive element in blood as the resistive element is heated. Use of conductive coatings for a sacrificial anode can be avoided.

18 Claims, 4 Drawing Sheets

(51) Int. Cl.
*A61B 18/08* (2006.01)
*A61B 17/12* (2006.01)
*A61N 1/36* (2006.01)
*A61N 1/39* (2006.01)
*A61B 18/00* (2006.01)
*A61B 17/00* (2006.01)
*A61B 18/14* (2006.01)

(52) U.S. Cl.
CPC ........ *A61B 18/082* (2013.01); *A61N 1/36125* (2013.01); *A61N 1/3956* (2013.01); *A61B 2017/00132* (2013.01); *A61B 2017/00154* (2013.01); *A61B 2017/00159* (2013.01); *A61B 2018/0072* (2013.01); *A61B 2018/00083* (2013.01); *A61B 2018/00148* (2013.01); *A61B 2018/00345* (2013.01); *A61B 2018/00577* (2013.01); *A61B 2018/00589* (2013.01); *A61B 2018/00702* (2013.01); *A61B 2018/00767* (2013.01); *A61B 2018/00821* (2013.01); *A61B 2018/1435* (2013.01)

(58) Field of Classification Search
CPC ........... A61B 2017/00154; A61B 2017/00159; A61B 2018/00083; A61B 2018/00148; A61B 2018/00345; A61B 2018/00577; A61B 2018/00589; A61B 2018/00702; A61B 2018/0072; A61B 2018/00767; A61B 2018/00821; A61B 2018/1435
See application file for complete search history.

(56) References Cited

U.S. PATENT DOCUMENTS

| | | | |
|---|---|---|---|
| 5,433,708 A * | 7/1995 | Nichols | A61B 18/082 604/113 |
| 5,851,206 A * | 12/1998 | Guglielmi | A61B 17/12022 606/28 |
| 6,007,570 A * | 12/1999 | Sharkey | A61B 17/1671 606/15 |
| 6,019,877 A | 2/2000 | Dupelle et al. | |
| 6,176,856 B1 | 1/2001 | Jandak et al. | |
| 6,189,536 B1 | 2/2001 | Martinez et al. | |
| 6,393,314 B1 | 5/2002 | Watkins et al. | |
| 7,572,257 B2 * | 8/2009 | Whayne | A61B 18/148 606/28 |
| 7,638,032 B2 | 12/2009 | Zhou et al. | |
| 8,010,191 B2 | 8/2011 | Zhu et al. | |
| 8,491,761 B2 | 7/2013 | Borregaard | |
| 8,623,097 B2 | 1/2014 | Gerold et al. | |
| 9,351,785 B2 | 5/2016 | Hong et al. | |
| 2007/0073282 A1 | 3/2007 | McGaffigan et al. | |
| 2008/0027428 A1 * | 1/2008 | Palanker | A61B 18/1402 606/45 |
| 2008/0283417 A1 | 11/2008 | Zhou et al. | |
| 2008/0319501 A1 | 12/2008 | Zhu et al. | |
| 2010/0010640 A1 | 1/2010 | Gerold et al. | |
| 2011/0180421 A1 | 7/2011 | Borregaard | |
| 2011/0224669 A1 * | 9/2011 | Podany | A61B 18/148 606/48 |
| 2012/0172864 A1 * | 7/2012 | Farin | A61B 18/14 606/33 |
| 2013/0178910 A1 * | 7/2013 | Azamian | A61B 17/00234 607/33 |
| 2015/0094704 A1 | 4/2015 | Hong et al. | |

OTHER PUBLICATIONS

Examination Report for GB1522353.0 dated Apr. 11, 2017 (4 pages).
GB Examination Report for GB1522353.0, dated Apr. 11, 2017.
GB1522353.0 dated May 25, 2016—Combined Search and Examination Report.

* cited by examiner

ELECTROCHEMICAL PROTECTION OF CONDUCTING CIRCUIT IN THE BODY OF A PATIENT

CROSS-REFERENCE TO RELATED APPLICATIONS

This application claims the benefit of priority under 35 U.S.C. § 119(a) to Great Britain Patent Application No. GB 1522353.0, filed Dec. 18, 2016, which is hereby incorporated by reference in its entirety.

TECHNICAL FIELD

The present invention relates to apparatus and a method of providing electrical power in the body of a patient and to apparatus and a method of protecting an electrically operated heating circuit in the body.

BACKGROUND OF THE INVENTION

There are instances where it is desirable to insert or implant into the body of a person an electrically conductive circuit, in particular a conducting wire. Examples may be to provide heating, an electrical connection between implanted components, an antenna or as any other electrical conduction part of a device. Electronic circuits used in the human body are typically isolated from the person's blood, tissue or interstitial fluids by physical barriers such as with coatings, sleeves, envelopes and so on. The present invention, described below, proposes the use of a bare electrical conductor and associated power supply system.

It is often necessary or desirable to occlude a body vessel. There are numerous known techniques to achieve this, the most invasive typically being by ligation of the vessel from outside. A number of endoluminal procedures are also known, such as by implantation of vascular plugs, embolization coils or particles, as well as by electrical methods including RF embolization. Implantation of a vessel blocking device, such as a coil or plug, leaves within the patient's body a foreign object, which can result in complications. Furthermore, the implanted device may not provide proper occlusion and/or may move over time, losing occlusive efficacy. RF embolization has been the subject of numerous studies. In particular two principal systems have been investigated, the first being a monopolar system in which a conductor providing an anode is placed endoluminally at the location at which it is desired to ablate the vessel, and a conductor providing a cathode pad is placed adjacent the patient, at a location as close as possible to the anode. The second system is a bipolar system in which both the anode and the cathode conductors are disposed in the vessel to be treated, for instance by being disposed on a common endoluminal carrier. RF embolization relies on passing current at RF frequencies through the electrode of the system and use of ionic conduction through the patient's blood or tissue. The RF energy causes heating of the blood or tissue and ablation either by generation of a blood clot or by collapse of the vessel due to the ablation energy. In theory such a system can work effectively, however, it does suffer from drawbacks. During the RF ablation process blood (or tissue) coagulates around the anode. Once this occurs the coagulation creates a current barrier with a resultant loss of ablation function. If ablation up to that point has not been sufficient to close the vessel, there will be incomplete occlusion. For this and other reasons, RF energy is supplied at a power high enough to seek to ensure that sufficient blood or vessel tissue is ablated to create a good enough seal of the vessel. However, this can result in an excess of energy and an excess of heating being applied to the vessel, with the risk that there can be damage to the vessel and/or nearby organs. For these and other reasons, RF ablation has had mixed results.

Examples of some prior art implantable conductive circuits are described in US-2011/0180421, U.S. Pat. Nos. 6,019,877, 6,189,536, US-2008/0283417, US-2010/0010640 and US-2008/0319501.

SUMMARY OF THE INVENTION

The present invention seeks to provide a conductive circuit and medical apparatus for location within a person and a system and method for driving and protecting such a circuit. The preferred embodiments are directed to improved vessel ablation apparatus and in particular a resistive ablation system.

According to an aspect of the present invention, there is provided medical ablation apparatus as in claim 1.

Resistive vessel ablation has not traditionally been considered and efforts in the art have focused on ablation by RF means. A resistive terminal can suffer from electrochemical corrosion as it is heated during use, leading to deterioration of the terminal and loss of elements into the blood stream. These problems can in theory be mitigated by coating the conductor with an electrically conductive insulator. However, the coating adds stiffness and bulk to the conductor and can also lead to a loss of heating efficiency, leading to longer procedure times and possible overheating of the coating.

The inventors have discovered that an efficient resistive ablation system can be provided by applying an alternating current through the resistive electrical terminal. This allows the terminal to heat as required but can reduce or eliminate corrosion of the terminal.

Advantageously, the power supply is configured to generate a balanced alternating current so that the sum of pulses is substantially zero.

In a preferred embodiment, the second end of the resistive heating terminal is disposed beyond the distal end of the insulating carrier element and the first end of the resistive heating terminal is disposed within or proximate the distal end of the elongate insulating carrier. In these embodiments, the second conductor extends beyond the distal end of the elongate insulating carrier and there may be provided an insulating sleeve covering the portion of the second conductor extending beyond the distal end of the elongate insulating carrier.

In some embodiments, the resistive heating terminal is coil shaped.

The carrier element may be a catheter with at least one lumen through which the non-resistive conductors may pass.

In the preferred embodiment, the resistive electrical terminal has a resistance between 10 and 100 ohms. Advantageously, the power supply is configured to generate a power in the resistive electrical terminal of at least one Watt, in some embodiments of around 10 Watts but in some cases up to around 40-50 Watts.

It has been found that it is advantageous to configure the power supply to generate an alternating current through the resistive electrical terminal at a frequency of at least 60 Hz, in some embodiments of up to 100 Hz, more preferably of around 500 Hz or above. At 2 kHz nerve stimulation ceases and in some applications it may be preferable to provide the resistive heating at frequencies above 2 kHz.

Preferably, the power supply is configured to generate a current at a constant voltage between 2 to 42 volts.

In some embodiments, the power supply is configured to generate a square wave alternating current through the resistive electrical terminal. In other embodiments, the power supply is configured to generate a tapering wave alternating current through the resistive electrical terminal.

Preferably, the power supply includes a timing element and is operable to supply current through the resistive electrical terminal for up to 30 minutes, although this may be as little as up to 2 minutes.

In the preferred embodiment, the distal (operative) portion of the resistive electrical terminal is bare.

Advantageously, the distal portion of the resistive electrical terminal is made of a nickel and chromium alloy.

Other aspects and advantages of the device, system and method taught herein will become apparent from the description which follows.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Described below are embodiments of vessel ablation apparatus incorporating the concepts taught herein. More specifically, the apparatus occludes a vessel by heat ablation, principally by collapsing the vessel and causing blood to clot at the distal end of the apparatus. The blood clot forms a plug to occlude the vessel.

The embodiments described below and the accompanying drawings set out in detail the primary components of the apparatus, relevant to the teachings herein. The person skilled in the art will readily appreciate there are other elements and characteristics to the apparatus which will be incorporated in a practical implementation, such as the structure of the delivery catheter, of the deployment handle, materials used and so on. These are all part of the common general knowledge and are therefore not described in further detail herein.

The drawings are schematic only and in practice the apparatus, and in particular the distal end of the device, would have a form suitable for the intended application and the vessel the device is designed to treat. Generally speaking, the apparatus will have, at least in its portion which is fed endoluminally into the patient, as small a diameter as feasible in order to optimise trackability in the patient's vasculature and in order to be able to treat small diameter vessels.

Figure 1:
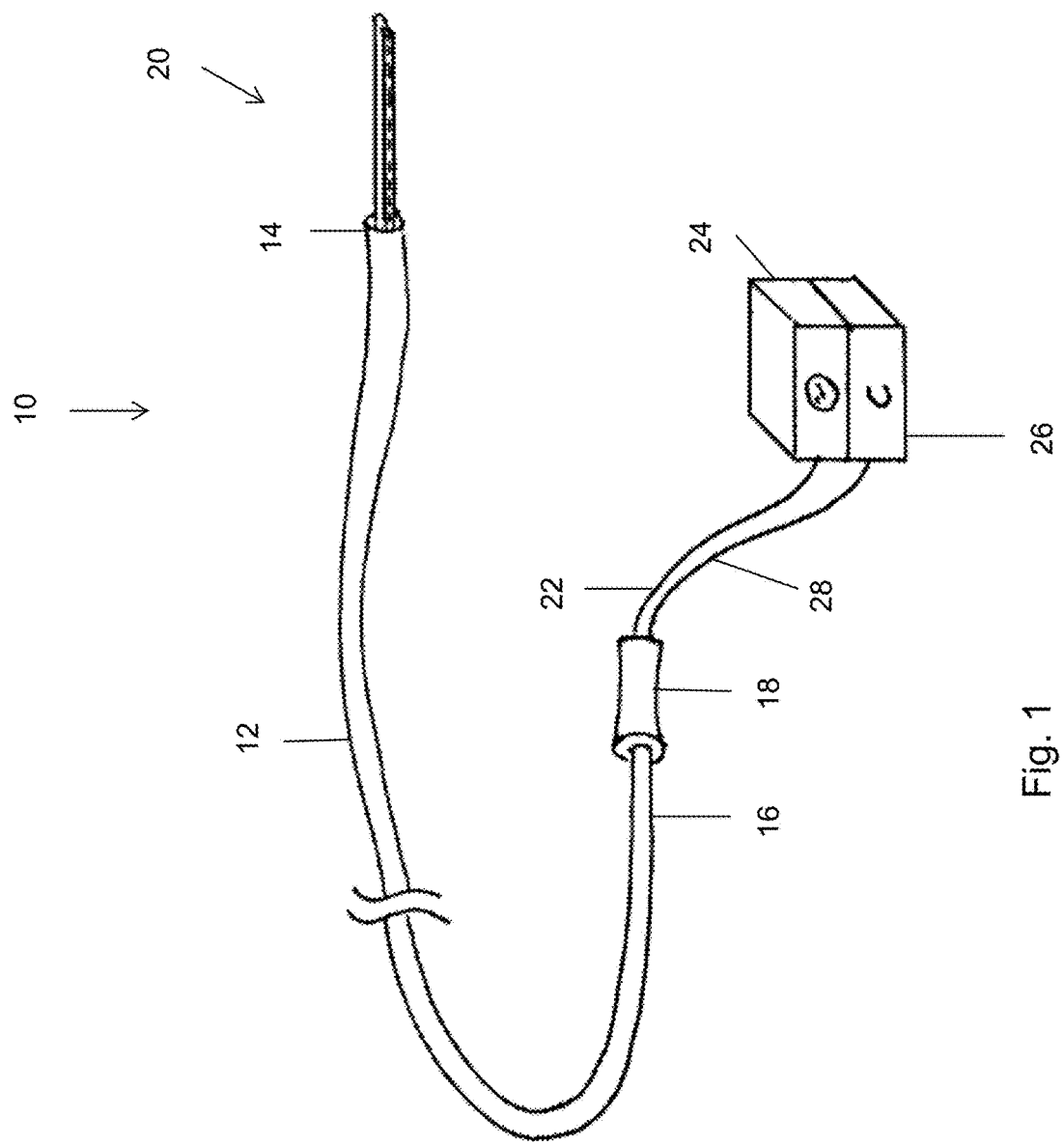
FIG. 1 is a schematic diagram of an embodiment of vessel ablation apparatus according to the teachings herein.

Referring first to FIG. 1, this shows in general form an embodiment of vessel ablation system incorporating the teachings herein. It is to be understood that the term "vessel ablation system" as used herein is primarily intended to refer to a system which heats a segment of a vessel in order to cause coagulation of the blood to form an occluding plug. For this purpose, the distal end of the apparatus 10, and in particular the electrical terminal or terminals thereof, are made of a relatively soft and flexible material able to curve in a vessel. It is preferred also that the tip of the apparatus is blunt so as not to pierce into the wall of the vessel. It is not excluded, however, that other embodiments of the apparatus 10 can be designed to effect vessel ablation by heating the vessel wall itself, causing contraction of the vessel and occlusion in this manner. For such a purpose, the distal end of the apparatus 10 and in particular the electrical terminals may be made of a more rigid material able to penetrate into vessel tissue and potentially with a sharp or pointed tip to facilitate the piercing of the vessel tissues.

The embodiment of apparatus 10 shown in FIG. 1 includes an elongate carrier catheter 12 having a distal end 14 and a proximal end 16. The distal end 14 is intended to be disposed within a patient's vessel at the point of treatment, whereas the proximal end 16 is intended to remain outside the patient's body during the medical procedure. The catheter 12 generally has a elongate form, long enough to pass from a remote percutaneous entry point and will typically have a length from tens of centimetres to a metre or more.

At the proximal end 16 there is typically provided a handle 18 for manipulation by a physician and this may or may not include elements able to slide the electrical terminal 20, described in further detail below, into and out of the catheter 12 as desired. In other embodiments, the electrical terminal 20 is fixed in relation to the catheter 12. The handle 18 may have any shape or form convenient for the purpose. Suitable handles of this nature are known in the art and therefore not described in detail herein.

Attached to the handle 18, in particular to conductors leading to the electrical terminals at the distal end 20 of the apparatus 10, are at least electrical conductors 22 (typically feed and return conductors) which are coupled to the resistive electrical terminal at the distal end 20 of the apparatus 10, described in further detail below. The wires 22 are connected to an alternating current source 24.

The apparatus 10 preferably also includes a control unit 26 for controlling the power supply 24 and this may include additional wires 28 leading to the distal end 20 of the apparatus for control functions and for feedback, such as for temperature sensing and the like. The control unit 26 may include a timing element, a memory for storing a database of suggested or programmed heating times and other components.

In some embodiments, the power supply and the control unit may be incorporated within the handle 18, whereas in other embodiments these may be provided in separate units connected to the handle 18 by the wires 22, 28. The power supply unit 24 and, where provided, the control unit 26 may be powered by mains power or by battery power. In the latter case in particular the units 24, 26 can be self-contained, such as in an appropriate handle 18.

The conductive elements at the distal end 20 of the apparatus 10 include a resistive element and, in this embodiment, a non-resistive conductor which extends to the tip of the assembly 10. It is to be understood that the term "non-resistive conductor" is used herein to denote a conductor which has negligible resistance, particularly compared to the resistance of electrical heating terminal of the apparatus. A conductor with negligible resistance will exhibit no or virtually no voltage drop cross the conductor element during use and therefore no active heating as a result of current passing through the conductor.

Figure 2:
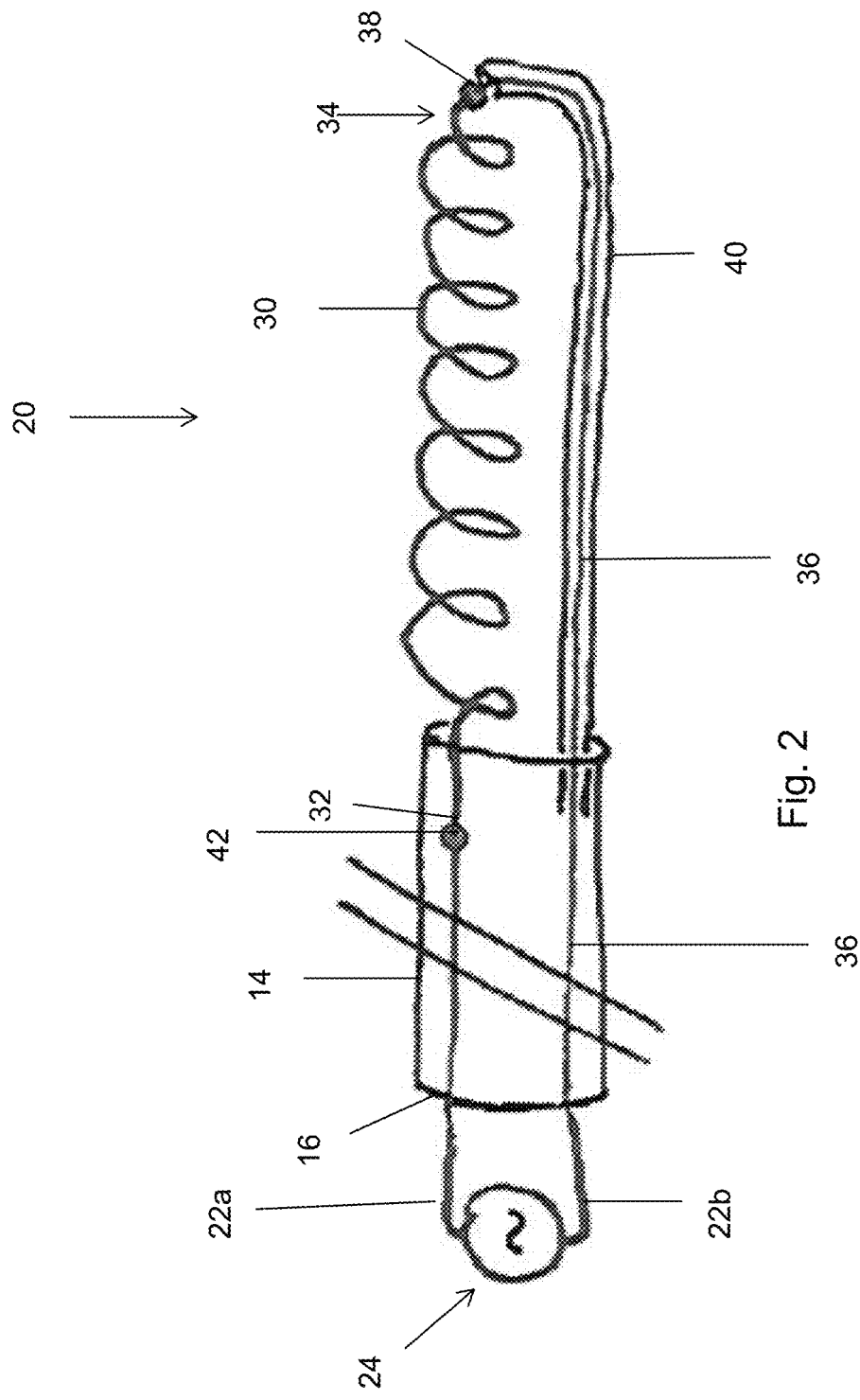
FIG. 2 is an enlarged schematic view of the distal end of the ablation apparatus of FIG. 1.

With reference now to FIG. 2, this shows an enlarged view in schematic form of a preferred embodiment of the electrical terminal structure at the distal end 20 of the apparatus 10. It includes a resistive electrical terminal 30 which is shown in coiled form and which has a proximal end 32 and a distal end 34. There is also included a non-resistive conductor 36 which extends to the distal end 34 of the resistive terminal 30 and is attached thereto at an attachment point 38, which may be a solder joint. The non-resistive conductive element 36 is, in this arrangement, covered by an insulating sleeve 40 in order to prevent shorting with the resistive terminal 30. It will be appreciated that the resistive terminal 30 and non-resistive conductor 36 will typically be provided on a support element, which may be a rod, catheter, guide wire element or any other support element which enables the distal end 20 to retain its shape in a vessel and when fed through the vasculature up to the treatment site. The person skilled in the art will be able to identify structures suitable for achieving this purpose. It is not excluded that in some embodiments the sleeve 40 may act as the support. The resistive terminal 30 could, in some embodiments, be wound around the sleeve 40 for support.

The resistive element 30 is preferably uncoated and thus bare, that is of bare metal or metal alloy.

The proximal end 32 of the resistive element 30 is disposed within the catheter 14 and may extend within an appropriate lumen in the catheter 14 or may be embedded within the wall material of the catheter 14. Similarly, the non-resistive conductor 36 extends through the catheter 14 and again may be disposed within a lumen of the catheter 14 or embedded within the wall material of the catheter 14. For this purpose, the catheter 14 is made of a non-conductive material, for instance any of the materials commonly used for catheters, pusher elements and so on.

In the embodiments shown, there is provided a non-resistive conductor wire 22a extending from the proximal end 16 of the catheter 14 to the proximal end 32 of the resistive element 30 and attached to the resistive element 30 at a connection point 42, which may be a solder joint.

The resistive electrical terminal 30 may have a resistance of between 10 and 100 ohms, with a resistance of around 90 ohms or so being found to be particularly effective. The resistive element 30 may have any length suitable for the intended purpose and this is particularly dependent upon the length of the occluding barrier which it is desired to create. The resistive element 30 will typically have a greater length for larger vessels and for vessels with greater blood flow, and a shorter length for shorter vessels and for those were blood flow is relatively low. In practice, the resistive element may have a length from a few millimetres to a centimetre or two, or more.

The power supply 24 is designed to generate power in the resistive electrical terminal 30 of at least 1 Watt, although in other embodiments this could be higher, for example up to 10 Watts or so. It has generally been found that it is rarely necessary to use a power greater than 40-50 Watts.

The power supply 24 is arranged to feed an alternating current through the resistive terminal 30, preferably at a frequency at least 60 Hz or 100 Hz, although greater frequencies may be used, for example of around 500 Hz or more, or even around or slightly above 2 kHz.

It is preferred that the power supply 24 generates current at a constant voltage in a range from about 2 to about 42 volts, the voltage typically being dependent upon the power desired to be generated at the resistive element 30.

In practice, the apparatus 10, that is power supply 24, can create an occlusive barrier by ablation of blood within a time of around 2 minutes, although for larger vessels and higher flow rate vessels, this may take up to around 30 minutes or so.

The resistive electrical terminal 30 may be made of any suitable material, although it is preferred that this is an alloy of nickel and chromium. Other examples include an alloy of iron, chromium and aluminium, such as Kanthal™; or of cobalt, chromium and iron, such as Elgiloy™.

Figure 3:
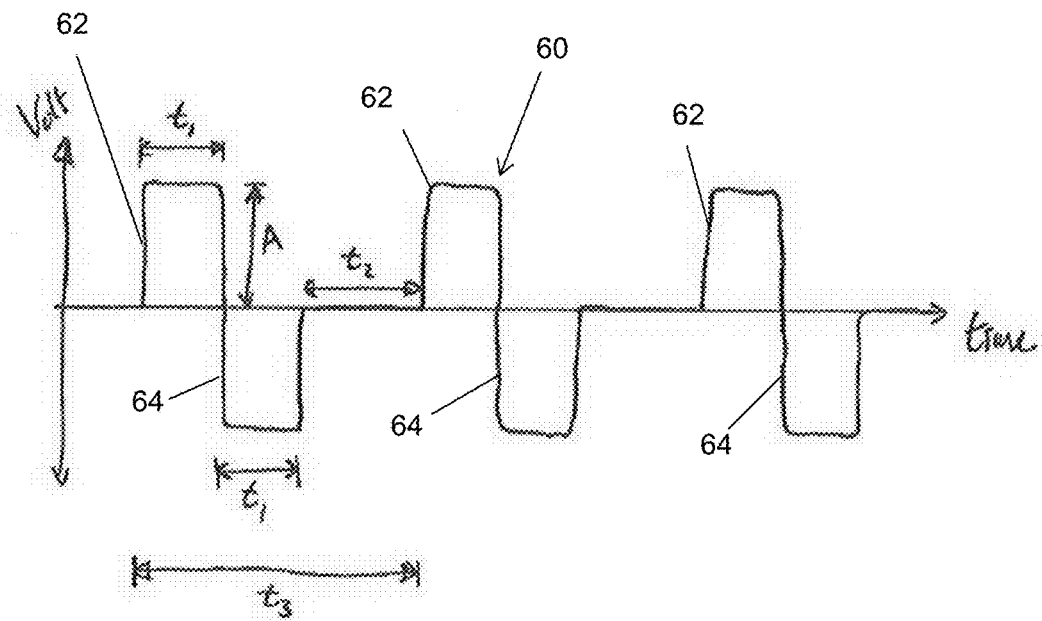
FIG. 3 is a graph showing one embodiment of an embodiment of a.c. current flow through the resistive terminal of the apparatus of FIGS. 1 and 2.

Referring now to FIG. 3, this is a graph showing one embodiment as to how the power supply unit 24 may be designed to operate in order to supply alternating current to the resistive electrode 30.

An issue which has been discovered with resistive heating within a vessel is that the voltage generated across the surface of the resistive element will cause an electrochemical reaction with the blood, leading to the generation of corrosive by-products and gasses (by electrolysis). As explained above, although this can be mitigated by coating the resistive element, the coating makes the device stiffer and can also result in a reduction of heating efficiency, leading to longer procedure times and possible over-heating of the coating material. The inventors have discovered that if the resistive heating element is fed with alternating current rather than direct current, the instance of reaction to the surrounding blood and tissue can be substantially reduced and in some circumstances eliminated completely. In tests, the inventors have discovered that by driving the resistive element 30 at a frequency of at least 60 Hertz, the amount of reaction in blood is substantially reduced. At frequencies of more than 100 Hertz, no visible reaction was seen. Increasing the driving frequency improves the stability of the electrode even further and at driving frequencies of around 500 Hertz no evidence of any reaction at all with blood was found. Higher frequencies may be used to overcome the issue of nerve stimulation, such as of around 2 kHz or more. In practice, by supplying an alternating current through the electrode and in particular one in which the direction of the current is evenly reversed, the anode/cathode ends of the resistive element 30 will switch with the reverse current through the element. When the frequency of reversal is sufficiently fast, surface reactions at the element may be minimised or cancelled, minimising or avoiding corrosion of the resistive element 30.

In one tested embodiment, the resistive element 30 was formed of a nickel/chromium alloy, specifically Inconel 625™. This was driven at frequencies which effectively minimise surface reactions, and preferably above 100 Hertz. The resistive element was usefully formed as a coil having a known resistance. The current was supplied by a fixed voltage power supply, preferred in all embodiments although it is not excluded that a varying voltage supply can be used. The supply voltage was fixed at a voltage within a range of 2 to 42 Volts.

In FIG. 3, the alternating pulse of the embodiment shown is a square wave balanced so that the sum of the pulses 62, 64 is zero. In the embodiment of FIG. 3, each pulse 62, 64 has a duration of a given time $t_1$, the positive and negative pulses thus having the same time duration. Given that the voltage supply is constant, power delivered during each pulse will therefore also be the same.

It is preferred that between each pair of pulses 62, 64 there is a fallow period $t_2$, where current is not supplied through the heating resistance 30. Following the pause $t_2$ the pulses 60 and 62 are repeated.

The sequence of pulses 62, 64 may continue for a minute or longer, typically for a total period of up to about 2 minutes. In some cases, however, the current may be supplied for a total time of up to about 30 minutes, dependent upon the nature of the vessel to be occluded and the rate of blood flow through the vessel.

Figure 4:
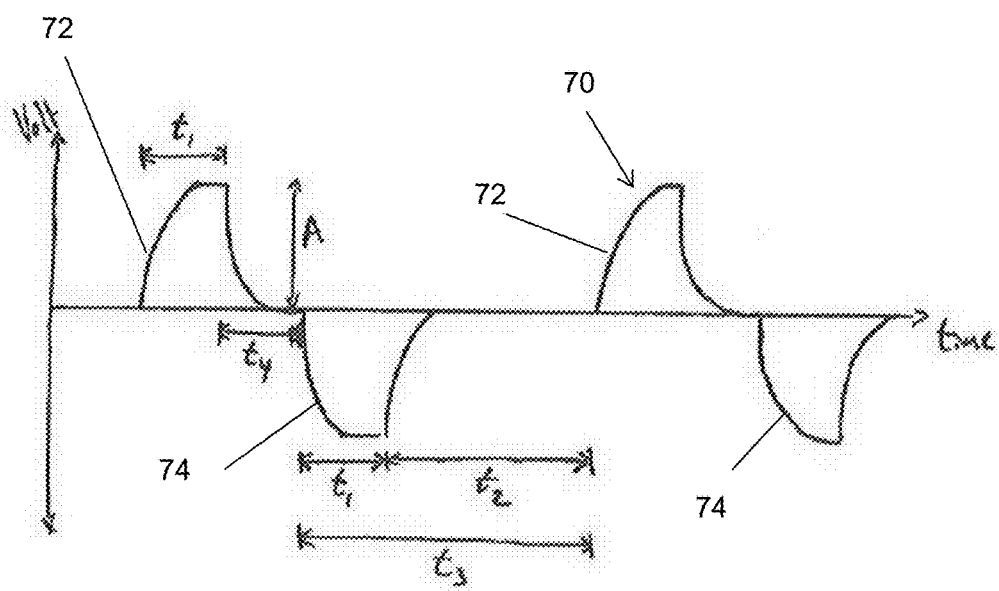
FIG. 4 is a graph showing one embodiment of another embodiment of a.c. current flow through the resistive terminal of the apparatus of FIGS. 1 and 2.

FIG. 4 shows another embodiment, in which a tapering wave alternating current is generated by the source 24, shown as graph 70 in the Figure. Again, the opposing pulses 72 and 74 have the same duration $t_1$ (from the start of the pulse up to and including a constant current period) and the same potential difference, with the pulses 72, 74 of each pair being offset relative to one another so as to have a net sum of zero. There may be a time lag of $t_4$ from the time at which the leading pulse 72 begins to tail off and the commencement of the following pulse 74. Furthermore, similar to the example of FIG. 3, there is preferably a fallow period $t_2$ from the moment the current of the trailing pulse 74 begins to tail off and the commencement of the next leading pulse 72. The time between the commencement of a trailing pulse 74 and the commencement of the next leading pulse 72 is, in this example, $t_3$ which equals to the sum of $t_1$ and $t_2$.

The total time over which sequences of pulse pairs 72, 74 continues, and similarly with the pulse of FIG. 3, is the total time deemed necessary to occlude the vessel being treated. As explained above, this may be for a minute or more, up to 2 minutes or even up to 30 minutes.

During periods when no current is supplied temperature at the distal end of the device can be usefully measured, typically by means of a thermocouple. In some embodiments, the resistive element 30 could also be used for the thermocouple.

The alternating current pulses may be formed by switching a single power supply through a H-bridge configuration or an LC charge/discharge circuit. In other embodiments, the power may be varied through pulse width modulation. In preferred embodiments, the pulse preferably has a $1/t_3$ cycle frequency, with $t_1$ being the single phase pulse width and $2*t_1/t_3$ being the duty cycle. The two opposing pulses may be separated by a pause $t_4$ to allow safe switching of a H-bridge or charging of a LC circuit.

Figure 5:
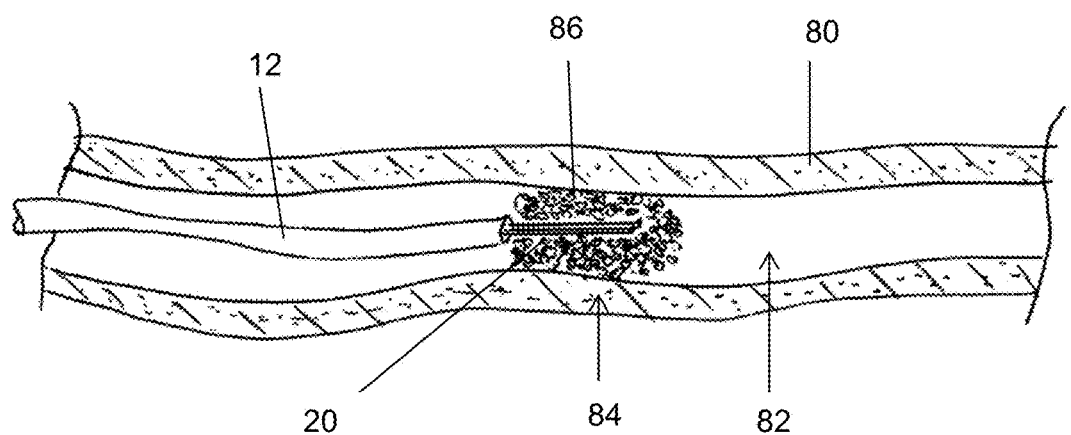
FIG. 5 is a schematic diagram showing the apparatus of FIGS. 1 and 2 in use in occluding a vessel by ablation.

Referring now to FIG. 5, there is shown in schematic form a portion of an exemplary blood vessel 80 having a vessel lumen 82. The ablation device is shown deployed within the vessel 80 and in particular with its distal terminal end 20 located at a portion 84 of the lumen 80 at which it is desired to create an occlusion barrier. The ablation apparatus 10 is operated in a manner described above, by feeding an alternating current through the resistive element 30 at the distal terminal end 20. The resistive element 30 will heat as a result of current passing through it, causing the surrounding blood to heat and coagulate into a blood clot 86 as depicted in FIG. 5. The ablation apparatus 10 is switched off once sufficient blood has coagulated to form an occlusion barrier within the vessel 80, at the location 84. As explained above, this may be from anything from a minute or 2 to 30 minutes or so depending upon the size of the vessel 80 (its cross-sectional area) and the speed of flow of blood through the vessel lumen 82. For smaller vessels and vessels where there is slower flow of blood, treatment times can be lower, whereas for larger vessels and vessels having a greater blood flow treatment times will be longer. In practice, suitable treatment times can be determined by routine experimentation. These can then be provided to the physician or programmed into the control unit 26 in order to control the duration of the electrical pulses supplied by the power supply unit 24.

The apparatus may be provided with additional components, one example being a temperature sensor disposed at the distal end 14 of the apparatus for measuring temperature caused by the heating of the resistive element 30. Such a temperature measurement can provide a useful indication of the state of clotting of the blood and formation of a occlusion barrier. This could be used instead of or in addition to a look up table, for instance.

As explained above, applying an alternating current through the resistive element 30 can prevent corrosion of the resistive element 30 as it is heated in the blood plasma. This avoids the need for protective coatings, a sacrificial anode, and the like.

The teachings herein are not limited to ablation apparatus and could be used for a variety of other medical devices, including for instance nerve stimulation devices and implantable cardioverter defibrillators (ICDs).

The embodiments described above have a resistive element 30 which is in the form of a linear coil. This is not an essential configuration although is currently preferred. Other embodiments may have a non-linear element, including an element which curves over itself to have its ends adjacent or inside the catheter 12, and a non-coiled element. A coiled element increases concentration of heating.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. Medical ablation apparatus including:
   an endoluminally deployable elongate insulating carrier element, including a proximal end and a distal end;
   a resistive heating terminal disposed at the distal end of the elongate insulating carrier element, wherein at least a portion of the resistive heating element extends beyond the distal end of the carrier, the resistive heating terminal including first and second ends;
   first and second conductors connected respectively to the first and second ends of the resistive heating terminal, each of the first and second conductors including proximal ends disposed at the proximal end of the elongate insulating carrier element;
   a power supply connectable to the proximal ends of the first and second conductors, the power supply being configured to generate an alternating current in the resistive heating terminal to cause the resistive heating terminal to heat as a result of the resistance thereof, the alternating current reducing or minimizing electrochemical corrosion of the resistive heating terminal; and
   an insulating sleeve covering a portion of the second conductor extending beyond the distal end of the elongate insulating carrier element, the insulating sleeve being parallel to the resistive heating terminal and comprising a curved portion at a distal end of the insulating sleeve,
   wherein the second end of the resistive heating terminal is connected to a distal end of the second conductor proximate a distal end of the curved portion of the insulating sleeve, and
   wherein the resistive heating terminal is coiled form and the resistive heating terminal is bare.

2. Medical ablation apparatus according to claim 1, wherein the power supply is configured to generate a balanced alternating current.

3. Medical ablation apparatus according to claim 1, wherein the second end of the resistive heating terminal is disposed beyond the distal end of the insulating carrier element and the first end of the resistive heating terminal is disposed within or proximate the distal end of the elongate insulating carrier.

4. Medical ablation apparatus according to claim 1, wherein the power supply is configured to generate an alternating current in the resistive heating terminal for at least one minute.

5. Medical ablation apparatus according to claim 1, wherein the resistive heating terminal has a resistance between 10 and 100 ohms.

6. Medical ablation apparatus according to claim 1, wherein the power supply is configured to generate a power in the resistive heating terminal of at least one Watt.

7. Medical ablation apparatus according to claim 1, wherein the power supply is configured to generate a power in the resistive heating terminal of at least 10 Watts.

8. Medical ablation apparatus according to claim 1, wherein the power supply is configured to generate a power in the resistive heating terminal of up to 50 Watts.

9. Medical ablation apparatus according to claim 1, wherein the power supply is configured to generate an alternating current through the resistive heating terminal of at least 60 Hz.

10. Medical ablation apparatus according to claim 1, wherein the power supply is configured to generate an alternating current through the resistive heating terminal of at least 100 Hz.

11. Medical ablation apparatus according to claim 1, wherein the power supply is configured to generate a current through the resistive heating terminal of around 500 Hz or more.

12. Medical ablation apparatus according to claim 1, wherein the power supply is configured to generate a current at a constant voltage between 2 to 42 volts.

13. Medical ablation apparatus according to claim 1, wherein the power supply is configured to generate a square wave alternating current through the resistive heating terminal.

14. Medical ablation apparatus according to claim 1, wherein the power supply is configured to generate a tapering wave alternating current through the resistive heating terminal.

15. Medical ablation apparatus according to claim 1, wherein the power supply includes a timing element and is operable to supply current through the resistive heating terminal for up to 30 minutes.

16. Medical ablation apparatus according to claim 1, wherein the power supply includes a timing element and is operable to supply current through the resistive heating terminal for up to 2 minutes.

17. Medical ablation apparatus according to claim 1, wherein a distal portion of the resistive heating terminal is made of a nickel and chromium alloy.

18. Medical ablation apparatus including:
an endoluminally deployable elongate insulating carrier element, including a proximal end and a distal end;
a resistive heating terminal disposed at the distal end of the elongate insulating carrier element, wherein at least a portion of the resistive heating element extends beyond the distal end of the carrier, the resistive heating terminal including first and second ends;
first and second conductors connected respectively to the first and second ends of the resistive heating terminal, each of the first and second conductors including proximal ends disposed at the proximal end of the elongate insulating carrier element;
a power supply connectable to the proximal ends of the first and second conductors, the power supply being configured to generate an alternating current in the resistive heating terminal to cause the resistive heating terminal to heat as a result of the resistance thereof, the alternating current reducing or minimizing electrochemical corrosion of the resistive heating terminal; and
an insulating sleeve covering a portion of the second conductor extending beyond the distal end of the elongate insulating carrier element,
wherein the resistive heating terminal is bare, and
wherein the alternating current generated by the power supply includes opposing pulses such that the opposing pulses of each pair are offset relative to one another so as to have a net sum of substantially zero, and each pair of opposing pulses is spaced from an adjacent pair of opposing pulses by a fallow time period where current is not supplied.

* * * * *